(12) United States Patent  
Zahniser et al.

(10) Patent No.: US 7,587,078 B2
(45) Date of Patent: Sep. 8, 2009

(54) AUTOMATED IMAGE ANALYSIS

(75) Inventors: David Zahniser, Wellesley, MA (US); Kam Lin Wong, Bedford, MA (US); Jim Linder, Acton, MA (US); Douglas Tenney, North Reading, MA (US)

(73) Assignee: Cytyc Corporation, Marlborough, MA (US)

( * ) Notice: Subject to any disclaimer, the term of this patent is extended or adjusted under 35 U.S.C. 154(b) by 821 days.

(21) Appl. No.: 11/120,437

(22) Filed: May 2, 2005

(65) Prior Publication Data

US 2006/0245630 A1    Nov. 2, 2006

(51) Int. Cl.
*G06K 9/00* (2006.01)
(52) U.S. Cl. .................. 382/133; 382/190; 128/922
(58) Field of Classification Search ............... 382/100, 382/115, 116, 117, 118, 123, 124, 125, 181, 382/190, 194, 195, 155, 156, 159; 340/5.1–5.92; 351/204; 235/380; 902/3–6
See application file for complete search history.

(56) References Cited

U.S. PATENT DOCUMENTS

| | | | |
|---|---|---|---|
| 4,191,940 A * | 3/1980 | Polcyn et al. | 382/128 |
| 4,845,552 A * | 7/1989 | Jaggi et al. | 382/128 |
| 4,998,284 A * | 3/1991 | Bacus et al. | 382/133 |
| 5,485,530 A * | 1/1996 | Lakowicz et al. | 382/191 |
| 5,548,661 A * | 8/1996 | Price et al. | 382/133 |
| 5,764,792 A | 6/1998 | Kennealy | |
| 6,208,749 B1 * | 3/2001 | Gutkowicz-Krusin et al. | 382/128 |
| 6,438,261 B1 * | 8/2002 | Moshe et al. | 382/133 |
| 2002/0081014 A1 | 6/2002 | Ravkin | |
| 2003/0048933 A1 * | 3/2003 | Brown et al. | 382/128 |
| 2004/0245350 A1 | 12/2004 | Zeng | |

FOREIGN PATENT DOCUMENTS

EP       0 311 368 A2    4/1989
EP       0 311 368 A3    4/1989

OTHER PUBLICATIONS

PCT International Search Report for PCT/US2006/015720. Applicant: Cytyc Corporation, Form PCT/ISA/210, dated Apr. 25, 2006 (4 pages).
PCT Written Opinion of the International Searching Authority for PCT/US2006/015720, Applicant: Cytyc Corporation, Form PCT/ISA/237) dated Apr. 25, 2006 (5 pages).

* cited by examiner

*Primary Examiner*—Anand Bhatnagar
(74) *Attorney, Agent, or Firm*—Vista IP Law Group LLP

(57) ABSTRACT

One automated imaging process, as described herein, includes: a) obtaining digital images of objects in a biological sample; b) selecting a plurality of objects of interest from the digital images; c) obtaining multiple images of the selected objects of interest at a plurality of different wavelengths; d) combining one of said multiple images with a corresponding digital image to produce a combined image; and e) analyzing the combined image in order to characterize the biological sample.

3 Claims, 1 Drawing Sheet

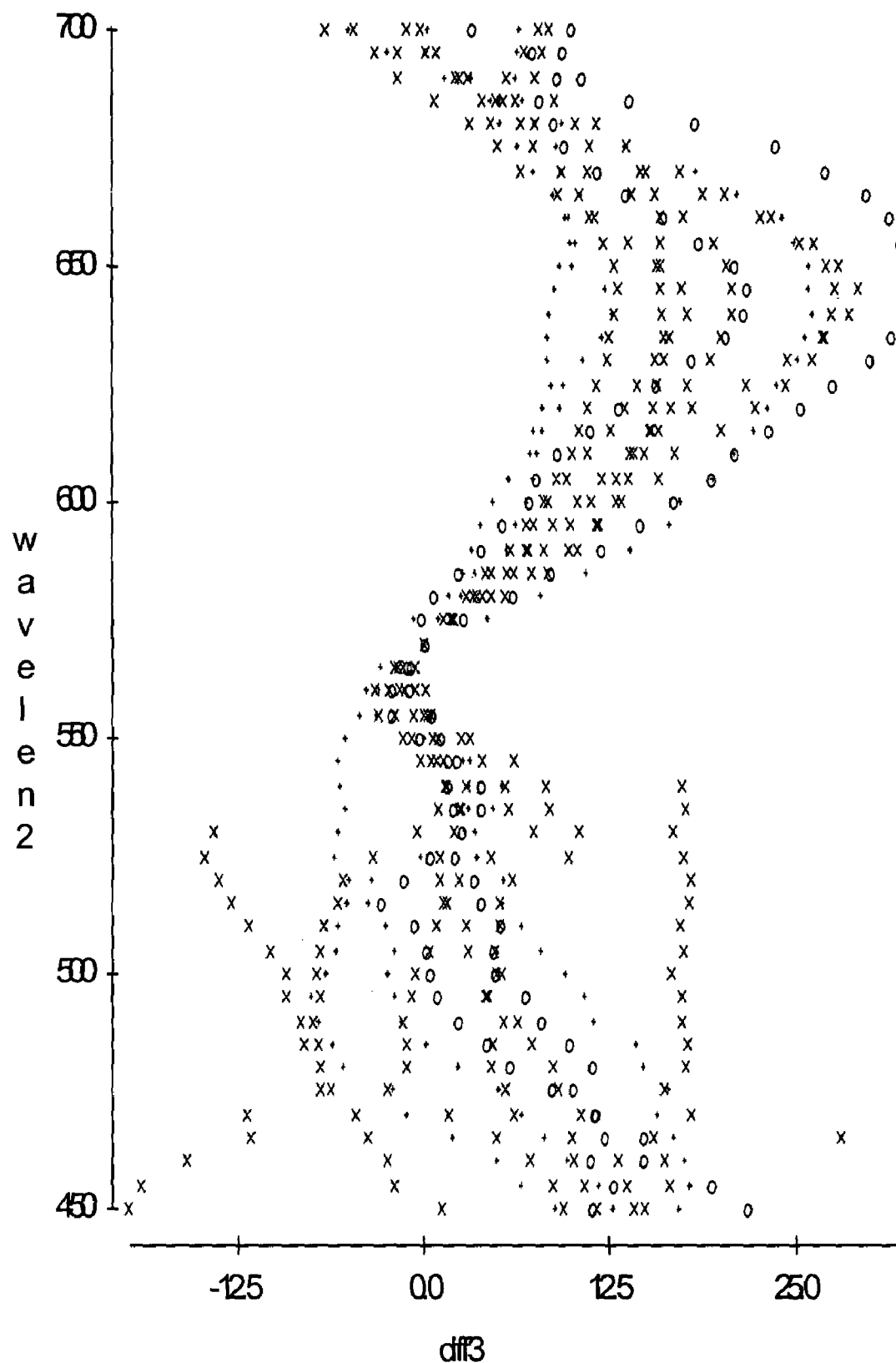

AUTOMATED IMAGE ANALYSIS

FIELD OF THE SUBJECT MATTER

The subject matter described herein relates to methods and devices useful in automated image analysis.

BACKGROUND

Cytological imaging of medical specimens is a tedious but crucial tool for medical analyses. Automated cytological imagers have been developed to meet the need for more uniform cytological image analyses. Automated cytological imagers do not vary as greatly in their interpretations of slides, are less subject to fatigue, and can provide much greater throughput as compared to humans.

Several previously developed and some currently available automated systems are used in conjunction with additional human analysis, and are used to increase the number of samples assayed and to lessen the fatigue experienced by the human analyst. Automated screeners can be used to select from each sample, objects for further human review. This method can increase the sensitivity of such assays, as the machine may more readily and economically identify those objects of interest in each sample to be analyzed by a human.

However, automated imagers are limited by the sample and data provided to them and by their programming. Additionally, for computational reasons, imagers typically use monochromatic, black and white images for their analyses, whereas the sample itself may provide a great range of spectral data and other information, particularly for cytologically stained samples.

For example, in the automated image analysis of pap-stained samples, the classification of abnormal objects in a conventional automated screening system can be complicated by the presence of normal metaplastic cells and other confounding objects. Some imaging systems identify cells of interest in pap-stained specimens on the basis of their optical density, as they or their nuclei may appear "darker" (more optically dense) and/or larger than do normal cells in the specimen. Metaplastic cells in the stained specimen also have dark cytoplasms and consequently reduced nuclear:cytoplasmic contrast that may contribute to errors in measurement. The metaplastic cells can be quite numerous on a slide, while abnormal cells may appear infrequently, and thus automated imagers can undesirably select the metaplastic cells for human review as they appear equivalently dark to the imager but are much more numerous than the abnormal cells. The false selection rate of the frequently occurring but disease-negative metaplastic cells by the imager thus limits accurate disease detection.

SUMMARY OF THE SUBJECT MATTER

In accordance with one embodiment disclosed herein, an automated imaging process includes: a) obtaining digital images of objects in a biological sample; b) selecting a plurality of objects of interest from the digital images; c) obtaining multiple images of the objects of interest at a plurality of different wavelengths; d) combining one of said multiple images with a corresponding digital image to produce a combined image; and e) analyzing the combined image in order to characterize the biological sample.

In accordance with another embodiment disclosed herein, an automated imaging process includes: a) obtaining digital images of objects in a biological sample; b) selecting at least one object of interest from the digital images; c) obtaining at least one image of the at least one object of interest at a plurality of different wavelengths to form a set of multi-wavelength images; d) analyzing the set of multi-wavelength images in order to characterize the biological sample.

In accordance with yet another embodiment disclosed herein, an apparatus for use in a automated imaging process includes: a) at least one light source that can provide at least one spectral region to a sample; b) at least one detector that can detect at least one set of images of portions of the sample when illuminated by the at least one spectral region; and c) at least one computer that can select at least one subset of the images based on at least one set of criteria. If more than two sets of the images are collected, those images may be combined to form at least one combined image. Then at least one computer may also analyze the sets of images for the selected subset and can select a further subset of the sets of images based on a second set of criteria which may be the first set of criteria or a different set.

In accordance with still another embodiment disclosed herein, an apparatus for use in an automated imaging process includes: a) a first light source that can provide a first spectral region to a sample; b) a first detector that can detect first images of portions of the sample when illuminated by the first spectral region; c) a first computer that can select a subset of the first images based a first set of criteria; d) a second light source, which may be the first light source or a different light source, that can provide a second spectral region different from the first spectral region; e) a second detector, which may be the first detector or a different detector, that can detect a second image of the images in the selected subset when illuminated by the second spectral region; and f) a second computer, which may be the first computer or a different computer, that can produce a combined image comprising the second image and the first image for the selected subset and can select a further subset of the combined images based on a second set of criteria which may be the first set of criteria or a different set.

In accordance with a still further embodiment disclosed herein, an apparatus for use in an automated imaging process includes: a) a first light source that can provide a first spectral region to a sample; b) a first detector that can detect first images of portions of the sample when illuminated by the first spectral region; c) a first computer that can select a subset of the first images based a first set of criteria; d) a second light source, which may be the first light source or a different light source, that can provide a second spectral region different from the first spectral region; e) a second detector, which may be the first detector or a different detector, that can detect a second image of the images in the selected subset when illuminated by the second spectral region; and f) a second computer, which may be the first computer or a different computer, that can analyze the first and second images for the selected subset and can select a further subset of the first and second images based on second set of criteria which may be the first set of criteria or a different set.

BRIEF DESCRIPTION OF THE FIGURE

FIG. 1 depicts the incremental nuclear:cytoplasmic contrast levels for a dual wavelength (570 nm plus 2nd wavelength) combined image as compared to a single wavelength (570 nm) image, for 11 measured objects. Circle=normal intermediate cell, x=normal metaplastic cell, dot=abnormal cell.

DETAILED DESCRIPTION

Automated imaging processes and/or devices utilize multiple wavelengths of light to illuminate the sample and obtain images that can be manipulated automatically or by an operator, as described herein. Images that contain relevant information can also be obtained at different wavelengths in order to subject the combined image to additional analysis. In addition, objects found in one image can be subjected to different wavelengths of light in order to analyze the object in depth before rendering a diagnosis based on the sample. In some embodiments, relevant information can be obtained by illuminating the sample or specimen with white light and placing at least one color filter between the specimen/sample and at least one TV camera or other camera. A camera with switchable color filters may also be utilized. In some embodiments, an operator of the system may go back to the cell location, if a particular set of images comprises a "cell of interest", and produce or retrieve additional images to aid the researcher, computer or technician in completing the information about the sample or specimen.

Also provided herein are several methods, processes and devices of and for further investigating a set of objects by an automated imager, which methods, processes and devices may be used singly or in combination. Through the use of information obtained by analyzing objects at multiple wavelengths, cells or clusters containing features of interest ("positives") can be better distinguished from false alarm or negative cells in a selected set. Specific cell types, such as endometrial cells or endocervical cells, or cells of a certain abnormality, may also be identified through such interrogation.

A number of discrete imaging systems are commercially available as of the time that the application for the present patent was filed, including Cytyc Corporation's THIN-PREP® Imaging System, the TriPath FOCALPOINT™ Profiler, the ChromaVision ACIS® System, the CompuCyt iCyte Imaging System, the Applied Imaging CYTOVISION™ System, and the Veracel Verasys™ Imaging System. It will be appreciated that these apparatus and devices can be modified to incorporate additional imaging steps, such as those described herein.

The current THINPREP® Imaging System ("TIS") identifies fields of view having one or more objects of interest in a specimen sample slide, including both single cells and clusters, stained by a Papanicolaou staining process and digitally imaged. The TIS can compile a list, for example, of the 100 single objects on a given sample slide with the highest integrated optical density and a list of the 20 clusters with the highest average optical density. Other values of objects and clusters can be collected above or below the 100 and 20 values previously described. Additional analysis as provided herein improves discrimination, proper selection and improved analysis of these identified objects. This additional level of analysis is unique in that it is focused on identified objects and involves the use of spectral analysis.

Contemplated methods of identifying wavelength(s) of light allow for an improved categorization of a cytological sample involve scanning a sample throughout a spectral region and determining if particular wavelength(s) within that region allow for improved categorization of a sample parameter. The sample may be scanned at regular or irregular intervals throughout the spectral region, and then combined in different ways with an unmodified image and/or with one or more different wavelength-specific images. One portion of the sample may also be scanned at regular or irregular intervals throughout the spectral region with each wavelength-specific portion being reviewed automatically or by the user, thus creating multiple wavelength-specific images of the same portion of the sample.

A variety of different sample parameters may be analyzed to determine their affect on the ability to more accurately categorize an imaged sample. In some embodiments, it may be desirable to identify the border of the nucleus. The regularity of the shape of the nucleus can provide important clues as to the status of the imaged cell and an irregularity in the nuclear shape can indicate a pre-malignant status. Therefore an improved ability to identify the nucleus, for example, by increasing contrast between the nucleus and cytoplasm, would yield an improved method of automatically diagnosing the condition of the cells.

In some embodiments, imaging the nucleus of the cells includes determining the texture of the nucleus, its shape, the integrated darkness, the average darkness or a combination thereof. Texture refers to analyzing the value of a given pixel in comparison with neighboring pixels, as known in the art. Shape can be determined through any suitable technique, for example by determining the square of the perimeter divided by $4\pi$ times area. Additionally, the "ring" of cytoplasm surrounding the nucleus may also be used. The optical density of the cytoplasm in this ring may be subtracted digitally from the image to provide for increased ability to measure the nucleus and can allow for improved visualization in situations where the cytoplasm of different cells overlap each other in a sample.

Although the examples herein describe cytological samples stained by a Papanicolaou staining process, it should be understood that the methods described herein can be used in conjunction with samples stained by other suitable and/or conventional processes and/or materials. Contemplated staining methods include hematoxylin and eosin staining, Feulgen stain, DNA staining, stoichiometric staining, and counter-staining. In some embodiments, the methods may include or utilize samples which are not stained. Additionally, although the examples depict the use of the methods with regard to gynecological samples obtained from pap smears, any suitable biological sample may similarly be utilized in the methods described herein.

Where a combination is disclosed herein, it is to be understood that each sub-combination of the elements of that combination is also specifically disclosed and is within the scope of the subject matter. Conversely, where different elements or groups of elements are disclosed, combinations thereof are also disclosed. Where any element of the subject matter is disclosed as having a plurality of alternatives, examples of that subject matter in which each alternative is excluded singly or in any combination with the other alternatives are also hereby disclosed; more than one element of contemplated subject matter can have such exclusions, and all combinations of elements having such exclusions are hereby disclosed.

Unless defined otherwise or the context clearly dictates otherwise, all technical and scientific terms used herein have the same meaning as commonly understood by one of ordinary skill in the art to which this invention belongs. Although any methods and materials similar or equivalent to those described herein can be used in the practice or testing of the subject matter disclosed herein, the preferred methods and materials are now described.

As mentioned earlier, methods, process and/or apparatus described herein combine the ability of existing automated imaging systems, such as the TIS, with the additional capability to analyze an identified subset of "objects of interest" in a specimen sample in order to provide for the automatic recognition of normal cells, abnormal cells, particular disease-related conditions, or a combination thereof.

One automated imaging process, as described herein, comprises: a) obtaining digital images of objects in a biological sample; b) selecting a plurality of objects of interest from the digital images; c) obtaining multiple images of the objects of interest at a plurality of different wavelengths; d) combining one of said multiple images with a corresponding digital image to produce a combined image; and e) analyzing the combined image in order to characterize the biological sample.

In this contemplated embodiment, objects of interest are identified in the sample, and then additional images of these objects are obtained by illuminating the objects with other spectral regions. The additional images may be combined by any mathematical means, such as, e.g., additively, subtractively, and/or in a ratio in the combined image. More than two images may be combined. The combined images are then analyzed by a set of criteria as described herein, and the results are compared to those obtained from single-wavelength illumination. In this manner, additional useful illumination wavelengths can be identified. The additional images at a plurality of wavelengths may be acquired at the same time as the original image was acquired and then stored for later possible use. Or, objects may be relocated and new images at a plurality of wavelengths may then be acquired.

Another contemplated automated imaging process, as described herein, comprises: a) obtaining digital images of objects in a biological sample; b) selecting at least one object of interest from the digital images; c) obtaining at least one image of the at least one object of interest at a plurality of different wavelengths to form a set of multi-wavelength images; d) analyzing the set of multi-wavelength images in order to characterize the biological sample.

In this additional contemplated embodiment, at least one image collected at a plurality of different wavelengths is used to extract features from the images. For example a ratio of darkness in the red end of the spectrum divided by darkness in the blue end of the spectrum would be useful in characterizing the image taken from the biological sample. This contemplated embodiment is designed to provide multiple perspectives on the same image or collection of images from a biological sample. In related embodiments, the user might take 4 or 5 images and find that some weighted value of the pixels within the nuclei from the different images give a result that may indicate abnormality versus normalcy. This process would give a "spectral signature" of the images from the biological sample.

In some embodiments, the imager first identifies the specific subset based on the highest integrated optical density nuclei and the highest average optical density clusters. In an abnormal specimen the subset typically includes abnormal objects and some "false alarms." In a normal specimen the subset typically includes normal objects and also some "false alarms." The false alarms are due to the presence of reactive/repair types of cells or artifacts such as overlapping nuclei or normal objects with inherently low contrast between the nucleus and the cytoplasm.

In some embodiments provided herein, the imager returns to these identified objects and applies additional analysis or analyses to better sort true abnormal objects from reactive/repair type changes and/or from "false alarms." The additional analysis can include spectral analysis or marker detection, and can involve measurements taken from both the nucleus and cytoplasm of the cells.

In some embodiments disclosed herein, a spectral analysis is performed on a specific subset of objects, such as the top 2000 objects, the top 1000 objects or less, such as the top 500 objects, the top 200 objects or the top 120 objects. The number of objects chosen for the subset is a function of such things as the computer memory, computer speed and the need of the user to characterize the sample with increasing accuracy. Once the subset of objects is selected and stored, an analysis of the top 120 images or objects from that subset can be selected based on suitable criteria. So, for example, a subset of objects may contain 2000 images taken at one wavelength. At another wavelength, 1000 images are collected. During analysis, 120 images are pulled from each of the 2000 image set and the 1000 image set.

In other embodiments, rather than returning to the subset of objects, images at a plurality of wavelengths may be stored at the time the initial images are acquired. Then additional analyses may be performed on the subset of objects of interest without relocating the object.

Multiple wavelengths of light can be used to digitize black and white images taken at a single or multiple wavelengths. The resulting "color" images may be more easily characterized than a single black and white image. In some embodiments, a classification of the objects can then be attempted. Based upon the analysis of the identified objects, a decision can made to identify a specimen as normal without requiring any additional review by a human.

Spectral information can also be used to identify specific types of cells. For example, in identifying a list of clusters it would be desirable to identify endometrial cells, or endocervical cells. In identifying a list of single nuclei, identification of metaplastic or endocervical cells or other specific cell types can be useful to the cytologist. In both types of identification, a certain level of abnormality can be determined through spectral analysis as provided herein. Such measurements can include nuclear and cytoplasmic measures of morphology and spectral information.

Spectral information can also detect certain cellular changes associated with disease or other cellular changes. For example, HPV infection may cause a cellular change that results in a spectral change. This can be detected by an imager, allowing the sample to be identified as being infected with HPV, without requiring a molecular assay.

Changes in cells due to the presence of disease or infection are often demonstrated by the presence of markers. For example, antibodies can detect the presence of an infection, for example an HPV or Chlamydia infection. Other molecular markers, such as nucleic acid probes or aptamers, can also be used to indicate the presence of disease or infection. In some embodiments, probes can be attached to a unique color label that is not normally present in the stain being used, for example a standard Pap stain. This label can comprise a certain absorption spectrum, or it may fluoresce only when a certain wavelength of light is used for illumination. The color analysis and/or illumination of the marker can be done on the identified objects.

Overall, this approach provides subsequent analysis of a reduced number of objects on the slide, which allows faster execution than can be obtained with a full slide analysis. It also allows for increased sensitivity or specificity since the additional analysis is only applied to objects that are already selected as suspicious due to perceived changes in a relevant property, for example nuclear density.

The TIS, for example, identifies the 100 objects (usually nuclei) with the highest integrated optical density (IOD). In a system utilizing a method provided herein, a spectral analysis can be made of some or all of those 100 identified objects. The spectral analysis can be used to give an indication of whether these are cell nuclei having spectral characteristics more similar to negative cell nuclei or to abnormal cell nuclei. Based upon this analysis a decision can be made that the slide is likely negative and no further human analysis may be required.

Other embodiments of automated spectral imaging methods include automated analysis of specimens for diagnosis, sorting, or selecting cells for additional analysis, for Pap tests, ductal lavage, lung, etc.; and improved segmentation analysis by combinations of images obtained from two or more colors of illumination. Also, automated methods may include steps involving multispectral unmixing, segmentation, and/or quantification of the images or objects of interest.

It is to be understood that terms such as "color(s)," "wavelength(s)" and "spectral region(s)" used herein can encompass both precise wavelengths with narrow bandwidths, for example as might be provided by a laser source, and somewhat broader bandwidths as may be provided, for example, by the use of filters with a broad- or multi-band light source. Light emitting diode (LED) illumination can provide either narrow or somewhat broader illumination, depending on the individual LED.

The sample, which also may be referred to as the specimen, that is analyzed can be any source of biological material that can be obtained from an organism directly or indirectly, including cells, tissue or fluid. Nonlimiting examples of the sample include blood, urine, semen, milk, sputum, mucus, pleural fluid, pelvic fluid, synovial fluid, ascites fluid, body cavity washes, eye brushing, skin scrapings, a buccal swab, a vaginal swab, a pap smear, a rectal swab, an aspirate, a needle biopsy, a section of tissue obtained for example by surgery or autopsy, plasma, serum, spinal fluid, lymph fluid, the external secretions of the skin, respiratory, intestinal, and genitourinary tracts, tears, saliva, tumors, organs, a microbial culture, a virus, and samples of in vitro cell culture constituents. The sample can be a positive control sample which is known to contain an object of interest.

The object of interest that may be selected by the automated device may be any component of the sample that is desired to be detected. Non-limiting examples of the object include a polynucleotide, a protein, a peptide, a polysaccharide, mucopolysaccharide, proteoglycan, a carbohydrate, a lipid, a fat, a cell, a cell type, an organism, a virus, a structure, an antigen, an inorganic compound, or other molecule to which a sensor can be obtained.

Exemplary molecular objects include HPV E2 protein, HPV E6 and E7 proteins, HPV L1 capsid protein, p16INK4a, E-cadherin, N-cadherin, p53, GCDFP-15, Pericyclin, NuMA, carbonic anhydrase, matrix metalloproteinases, nuclear matrix proteins, ferritin, aurora A, pericentrin, osteopontin, prostatin, insulin-like growth factor, fibroblast growth factor, BRCA1, BRCA2, mammoglobin, PSE, CEA, CA-125, CA 19-9, CA 15-3, somatostatin, synaptophysin, chromogranin, kallikriens, fibronectin, EGFR, K-ras, Her-2/neu, treponemal antigen, neuron-specific enolase, retinoblastoma protein, hepatitis C surface antigen, sexually transmitted disease markers including the outer membrane protein of *Chlamydia trachomatis*, cancer markers, and HIV gp120.

Where the object is a cell or cell component or product, the cell can be of any origin, including prokaryotic, eukaryotic, or archea. The cell may be living or dead. If obtained from a multicellular organism, the cell may be of any cell type. The cell may be a cultured cell line or a primary isolate, the cell may be mammalian, amphibian, reptilian, plant, yeast, bacterial, mycobacterial, spirochetal, or protozoan. The cell may be human, murine, rat, hamster, chicken, quail, or dog. The cell may be a normal cell, a mutated cell, a genetically manipulated cell, a tumor cell, etc.

In one embodiment for performing the automated imaging methods described herein, a device includes one or more light sources capable of illuminating the specimen at multiple wavelengths of light. The device also includes one or more detectors capable of obtaining images of the specimen at multiple wavelengths of illumination.

The device also includes a computer or other selection means capable of selecting a subset of objects of interest from images obtained from the specimen at a first wavelength. The device may select these objects based on any set of criteria, which may include one or multiple separate analyses. Examples of such criteria are provided herein, including average optical density, integrated optical density, shape, texture, etc. The device is capable of imaging the identified objects of interest at a second wavelength, and then combining these additional images with the first image of the objects to produce a combined image, which can then be subject to additional analyses to select a particular subset of the objects based on further criteria, which may be the same or different criteria as performed initially.

Images can be added together or compared to one another by analog devices or by digital devices. For example, two images may be added together by turning on two colors of illumination simultaneously (i.e. from two different wavelength LED's) and adding the images in an analog process. In other embodiments, the images may be digitized and added or compared.

EXAMPLES

The following examples are set forth so as to provide those of ordinary skill in the art with a complete description of how to make and use the subject matter described herein, and are not intended to limit the scope of what is regarded as the invention. Efforts have been made to ensure accuracy with respect to numbers used (e.g., amounts, temperature, etc.) but some experimental error and deviation should be accounted for.

Example 1

Screening for Multiple Wavelengths to Improve Automated Imaging

An experiment was performed to determine if imaging a sample at multiple wavelengths could enhance the operation of the scene segmentation and/or feature extraction operations on an automated imager. Some abnormal cells and many metaplastic cells have reduced nuclear contrast due to very thick cytoplasms. Additionally, some staining systems produce multiple colors in a stained sample, and a single color of illumination may not be optimal for all cells in the sample. For example, Papanicolaou staining can produce cells with red, blue or green cytoplasms, and a single wavelength as used with some digital imagers may not provide optimum imaging of such divergent cells. Therefore, overall improvement in contrast was used as one means to assess potential methods for improving analysis.

A set of eleven microscope fields containing normal, abnormal and metaplastic Papanicolaou-stained cells was digitized using 51 different wavelengths using a Zeiss Axioskop microscope with a black and white video camera. This was accomplished by placing a monochrometer (EG&G model 585-22) between the light source and the microscope. Images were then digitized at wavelengths between 450 and 700 nanometers, in steps of 5 nanometers. Once the multiple wavelength images were digitized, an algorithm was explored to add combinations of two images together, and then automatically determine contrast between cell nuclei and cytoplasms. Contrast was defined as the grey level difference of a 10×10 pixel box within the nucleus compared to a 10×10 pixel box within the cytoplasm. A single wavelength, 570 nm, was chosen that gave optimal contrast for most images.

Combinations of this image with the other wavelengths were analyzed to determine the change in contrast from the 570 nm image, for a combined image (the two images were added together and then divided by 2). FIG. 1 shows a scatterplot of the net change in contrast (diff3 on the x axis; diff3=the difference in grey values between nucleus and cytoplasm for the dual wavelength image, minus the difference in grey values between the nucleus and cytoplasm for the single wavelength image) for each of eleven objects for all 51 wavelength combinations (y axis) with the 570 nm image.

A range (between approximately 600 and 670) was identified where contrast was improved in the combined image for all objects, regardless of cytoplasmic color or cell type. This demonstrates that contrast can be improved combining images from multiple wavelengths.

Example 2

Multiple Wavelength Imaging Improves Analysis of Difficult Specimens

In order to explore the potential of using multiple wavelength imaging, a series of abnormal cells and normal metaplastic cells from Pap stained slides were digitized using a Zeiss Axioskop microscope with a black and white video camera using two wavelengths, 570 and 650 nm, selected based on Example 1. Full images were digitized to allow "confusion" of clusters, debris, blood, etc. The images were first analyzed using only a single wavelength—the standard green illumination used in many Pap test imaging systems (570 nm). The images were then analyzed using a combination of the two wavelengths 570 and 650 nm.

Cells were then automatically segmented to find the nuclei. The segmentation algorithm works by automatically finding potential nuclei (dark objects), and then uses an iterative method based upon the grey level histogram of the image. This method monitors changes in the minimum and maximum darkness values from a histogram of the grey levels within the current outline of the object. Many other segmentation methods can be applied to locate nuclei, cytoplasms or other objects in an image. After segmentation, features of the nuclei are extracted and a rejection of artifacts is done, based upon shape and texture measurements. In order to test the performance of the combined image, a simple listing of cells in order using the integrated optical density ("IOD") of the cells. This feature is one of the more discriminatory of all features measured on slides. However, difficulty has been encountered with "large/dark" but normal "metaplastic" cells appearing in positions in the list among the abnormal cells.

Patient samples with "troublesome" metaplastic cells were run and the 40 cells with the highest IOD were stored in a list. When only a single wavelength was used, metaplastic nuclei were appeared in the list among a set of abnormal nuclei characteristic of high grade squamous intraepithelial lesions, one at position 28 and more in positions 33 through 40. Many abnormal nuclei were found in the list of 100 nuclei with the highest integrated optical density.

When combined images from the two wavelengths were used to create the list of cellular IOD values from the same patient samples, however, of the first 40 nuclei the one and only metaplastic nucleus appeared in position 37. Now, more abnormal nuclei were shown in the first 40 position in the list. Thus, the combination demonstrated an ability to rank cells by providing fewer "false positive" nuclei in the top ranking and shows the usefulness of two color analysis with this very difficult problem.

As a final check, the images were analyzed for clusters by comparing data from matching clusters in the single wavelength and dual wavelength combined images. The data showed a significant improvement in the difference in standard deviation of grey levels between the "salt and pepper" appearance of white blood cell clusters and the smoother clusters (less variation in pixel density) of abnormal cells. This feature is important as it allows removal of "false alarms" due to white blood cell clusters. Without this discrimination, an imager may select some of the very numerous white blood cell clusters to show a cytotechnologist instead of the less frequent abnormal clusters that might be on the same slide. These data clearly indicate that contrast was improved, permitting better discrimination by the imager. Dual wavelength illumination allowed improved segmentation and classification in a clinical application with cells from Pap test slides.

Thus, specific embodiments, methods of use and applications of an improved automated image analysis system have been disclosed. It should be apparent, however, to those skilled in the art that many more modifications besides those already described are possible without departing from the inventive concepts herein.

What is claimed:

1. An apparatus comprising:
    a first light source that can provide a first spectral region to a sample;
    a first detector that can detect first images of portions of the sample when illuminated by the first spectral region;
    a first computer that can select a subset of the first images based a first set of criteria;
    a second light source, which may be the first light source or a different light source, that can provide a second spectral region different from the first spectral region;
    a second detector, which may be the first detector or a different detector, that can detect a second image of the images in the selected subset when illuminated by the second spectral region; and
    a second computer, which may be the first computer or a different computer, that can produce a combined image comprising the second image and the first image for the selected subset and can select a further subset of the combined images based on a second set of criteria which may be the first set of criteria or a different set.

2. The apparatus of claim 1, wherein the second computer, which may be the first computer or a different computer, can analyze the first and second images for the selected subset and can select a further subset of the first and second images based on a second set of criteria which may be the first set of criteria or a different set.

3. The apparatus of claim 1, wherein at least one of the first set of criteria or the second set of criteria comprises at least one wavelength.

\* \* \* \* \*

UNITED STATES PATENT AND TRADEMARK OFFICE
CERTIFICATE OF CORRECTION

PATENT NO. : 7,587,078 B2 Page 1 of 1
APPLICATION NO. : 11/120437
DATED : September 8, 2009
INVENTOR(S) : Zahniser et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1164 days.

Signed and Sealed this

Twenty-first Day of September, 2010

David J. Kappos
*Director of the United States Patent and Trademark Office*